(12) United States Patent
Krupa et al.

(10) Patent No.: US 10,815,166 B2
(45) Date of Patent: Oct. 27, 2020

(54) INTEGRATION OF AN ORGANIC CHLORIDE DECOMPOSITION REACTOR ON THE ISOMERIZATION/DEISOBUTANIZER C5 DRAG STREAM

(71) Applicant: UOP LLC, Des Plaines, IL (US)

(72) Inventors: Steven L. Krupa, Fox River Grove, IL (US); David J. Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 28 days.

(21) Appl. No.: 16/368,461

(22) Filed: Mar. 28, 2019

(65) Prior Publication Data

US 2020/0002248 A1   Jan. 2, 2020

Related U.S. Application Data

(60) Provisional application No. 62/691,539, filed on Jun. 28, 2018.

(51) Int. Cl.
| | |
|---|---|
| *C07C 5/22* | (2006.01) |
| *C07C 9/12* | (2006.01) |
| *C07C 9/14* | (2006.01) |
| *B01J 23/44* | (2006.01) |
| *B01J 23/42* | (2006.01) |
| *C07C 7/148* | (2006.01) |

(52) U.S. Cl.
CPC .............. *C07C 5/226* (2013.01); *B01J 23/42* (2013.01); *B01J 23/44* (2013.01); *C07C 5/2206* (2013.01); *C07C 7/148* (2013.01); *C07C 9/12* (2013.01); *C07C 9/14* (2013.01); *B01J 2523/824* (2013.01); *B01J 2523/828* (2013.01); *C07C 2523/42* (2013.01); *C07C 2523/44* (2013.01)

(58) Field of Classification Search
None
See application file for complete search history.

(56) References Cited

U.S. PATENT DOCUMENTS

| | | | |
|---|---|---|---|
| 2012/0024750 A1* | 2/2012 | Zhan | C10G 45/04 208/56 |
| 2013/0001133 A1* | 1/2013 | Zhan | C10G 29/26 208/97 |
| 2013/0062253 A1* | 3/2013 | Timken | C07C 5/277 208/64 |
| 2014/0171720 A1* | 6/2014 | Zhan | B01J 31/0289 585/852 |
| 2016/0002542 A1* | 1/2016 | Lacheen | C10G 29/04 585/324 |

* cited by examiner

*Primary Examiner* — Ali Z Fadhel

(57) ABSTRACT

A process for producing an isomerized product comprises sending a feed stream comprising butanes, hydrogen and an organic chloride to a butane isomerization reactor containing an isomerization catalyst to convert a portion of normal butanes in said feed stream to iso-butanes in an isomerized stream. The isomerized stream to a stabilizer column to produce a butane stream containing normal, iso-butanes and C5 hydrocarbons; the butane stream is sent to a column to produce an isomerized upper stream and a bottoms stream comprising a mixture of butanes, C5 hydrocarbons and organic chloride. The bottoms stream is sent to an organic chloride decomposition reactor to produce a mixture of HCl, hydrogen and hydrocarbons.

9 Claims, 1 Drawing Sheet

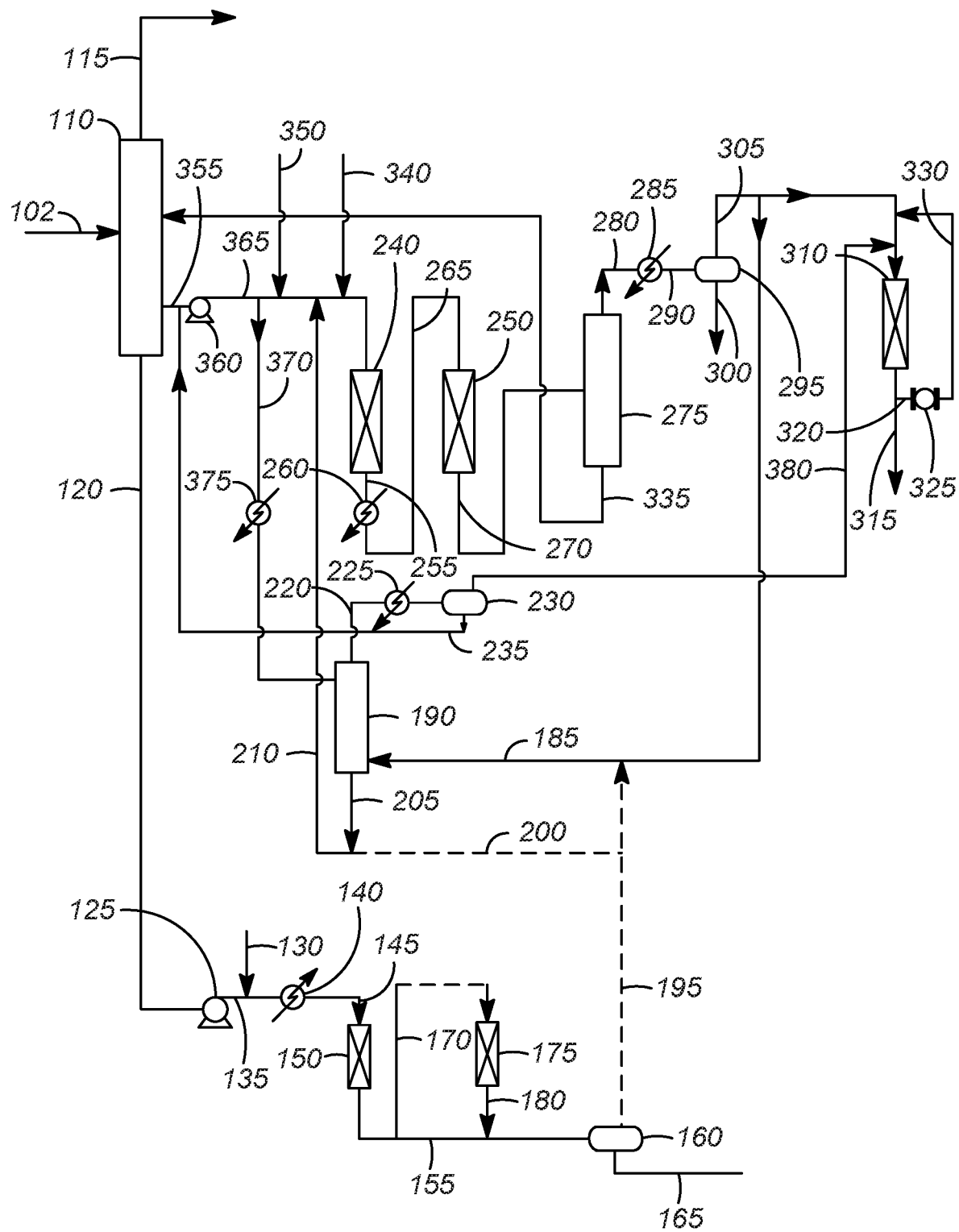

INTEGRATION OF AN ORGANIC CHLORIDE DECOMPOSITION REACTOR ON THE ISOMERIZATION/DEISOBUTANIZER C5 DRAG STREAM

RELATED APPLICATIONS

This application claims the benefit of U.S. Provisional Patent Application Ser. No. 62/691,539 filed on Jun. 28, 2018, the entirety of which is incorporated herein by reference.

BACKGROUND OF THE INVENTION

For almost a century, paraffin isomerization has continued to progress, beginning with the Friedel-Crafts aluminum chloride catalyst research and development during the Great Depression and the World War II need for high-octane jet fuel. It continued with the first commercialized butane isomerization process in the early 1940s, and the development of dual-functional catalysts and the first Butamer™ unit by UOP in the late 1950s, to the shale gas boom of the 2000s, and the current paraffin isomerization technologies and integration opportunities available for $C_4$, $C_5$-$C_6$, and higher paraffins. Yet, the final goal has remained the same: to produce higher-octane fuels.

Isomerization processes are widely used by many refiners to rearrange the molecular structure of straight chain paraffinic hydrocarbons to more highly branched hydrocarbons that generally have higher octane ratings. Many isomerization processes employ a chlorinated catalyst, such as chlorinated alumina catalyst, chlorinated platinum alumina catalyst, and the like, in a reaction zone (e.g., refers to an area including one or more reactors). The chlorinated catalyst requires a continuous addition of chloride to replace chloride removed from the surface of the catalyst and carried away in the reaction-zone effluent. Typically, a fresh feed of chloride promoter, usually an organic chloride such as perchloroethylene, is continuously introduced into a paraffin feed stream upstream from a reactor in the reaction zone. Inside the reactor, the chloride promoter decomposes to form hydrogen chloride that activates, e.g., promotes or regenerates, the catalyst by replenishing the chloride removed from the catalyst's surface.

As opposed to typical $C_5$-$C_6$ paraffin isomerization, where the isomerate is blended directly into the gasoline pool, the isobutane produced from a Butamer unit can be further reacted in the alkylation process to produce very high-octane alkylate, which is becoming a more important blending component enabling refiners to meet tightening fuel requirements in terms of aromatic content and Reid vapor pressure (RVP) concerns, especially where ethanol blending is mandated. Alkylate demand, and thus the demand for isobutane as its feedstock, also is increasing to compensate for lower-octane values in Fluid Catalytic Cracking (FCC) gasoline derived from paraffinic tight oil.

In addition, isobutane (iC4) is also a feedstock for the production of methyl tertiary butyl ether (MTBE), which is another high-octane gasoline blending component used in many parts of the world. In that process, $iC_4$ is dehydrogenated to isobutylene (through UOP's Oleflex™ process) and then converted into MTBE. Unconverted butenes and $nC_4$ are recycled to achieve essentially 100% conversion of the feed butanes to MTBE.

At the heart of the Butamer process are two fixed-bed reactors situated in a lead-lag configuration. The reactors contain chlorided platinum-alumina catalyst, which is contacted with the vaporized n-butane (nC4) feed, hydrogen gas, and a trace organic chloride injection (typically perchloroethylene, C2Cl4), all of which have been dried to ensure that water (a catalyst poison and corrosion enabler) is not introduced into the process. The organic chloride is converted to hydrogen chloride (HCl), which promotes and maintains the high activity of the catalyst, while the hydrogen gas aids the product selectivity toward iC4 by suppressing the polymerization of olefinic intermediates and essentially eliminates the formation of coke under normal operating conditions. In operation, it has been found that in some instances there is incomplete decomposition of the perchloroethylene as evidenced by the presence of 20-50 wppm PERC that is found in the process stream and in particular in a deisobutanizer bottoms C5 drag stream. While this C5 drag stream is relatively small compared to the size of the fresh feed, due to a concentration effect even trace levels of unconverted perchloroethylene is unacceptable. The C5 drag stream flow is small relative the fresh feed, such as ~1 wt % or less, and trace levels of any unconverted PERC in the Butamer reactor effluent concentrate in the C5 product. Because of this concentration effect there is a problem with unacceptable PERC level in the C5's despite achieving 99.83% or higher PERC conversion in the Butamer reactor. These C5 hydrocarbons then must either be purified or disposed of in some manner and may need to be sold at a deeply discounted price or even stored as unusable. Accordingly, it has now been found that the addition of a small reactor or reactor section to decompose the 20-50 wppm of unconverted PERC in the C5 drag stream can be effective to resolve this issue.

SUMMARY OF THE INVENTION

A butane isomerization process is provided in which a reactor is provided to decompose unconverted organic chloride into HCl. The invention remedies the problem that the organic chloride that is used as a source of chlorine for the catalyst in the isomerization reactor does not completely decompose in the isomerization reactor. The organic chloride, such as perchlorethylene is more difficult to remove from a hydrocarbon stream than its decomposition products. It has been found that placing a small reactor on a C5 drag line resolves the issue of the organic chloride in the hydrocarbons. The HCl that is formed can then be removed by a chloride guard bed or by other means and then the hydrocarbon stream, such as a C5 drag stream can then be used for other purposes

BRIEF DESCRIPTION OF THE DRAWING

The FIG. shows the integration of decomposition of the organic chloride on a C5 drag stream of a butane isomerization unit.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the hydrocarbon molecule. In addition, the term "Cn-Cn+1 hydrocarbon," such as "C5-C6 hydrocarbon," can mean at least one of a C5 and C6 hydrocarbon.

DETAILED DESCRIPTION OF THE INVENTION

The following Detailed Description is merely exemplary in nature and is not intended to limit the invention or the application and uses of the invention. Furthermore, there is no intention to be bound by any theory presented in the preceding background or the following detailed description.

Various embodiments contemplated herein relate to methods and apparatuses for isomerization of paraffins. Unlike the prior art, the exemplary embodiments taught herein introduce an isomerization reaction-zone effluent from an isomerization reaction zone to a stabilizer. The isomerization reaction-zone effluent comprises HCl, hydrogen, branched paraffins, and C5 to C7 hydrocarbons. As used herein, Cx means hydrocarbon molecules that have "X" number of carbon atoms, Cx+ means hydrocarbon molecules that have "X" and/or more than "X" number of carbon atoms, and Cx− means hydrocarbon molecules that have "X" and/or less than "X" number of carbon atoms. The stabilizer is operating at stabilization conditions effective to separate the isomerization reaction-zone effluent into a product stream that comprises the branched paraffins and a stabilizer overhead vapor stream that comprises HCl, hydrogen, and $C_{6-}$ hydrocarbons.

A butane isomerization process is provided in which a reactor is provided to decompose unconverted organic chloride into HCl. The HCl that is formed can then be removed by a chloride guard bed or by other means and then the hydrocarbon stream, such as a C5 drag stream can then be used for other purposes. While there may be other streams that can be treated in accordance with this invention, a smaller stream that has a concentration of organic chloride such as perchloroethylene is more easily treated to achieve the desired very low product chloride specification. It would be preferable if it was possible to improve the conversion of perchloroethylene within the butane isomerization reactor, but since there is already about 99.83% conversion and any change could impact upon isomerization performance. While it could be feasible to add a perchloroethylene decomposition reactor to the perchloroethylene feed stream to the prior art configurations, this would have a complication of high heat of reaction and a potential for undesired exotherms and possible perchloroethylene decomposition and adverse deactivation of the catalyst in the isomerization reactor. In addition, if makeup hydrogen is used for dilution of perchloroethylene for an upfront perchloroethylene decomposition reactor, there would be less hydrogen available, thus resulting in a higher exotherm in an upfront perchloroethylene decomposition reactor with a butane isomerization than a comparable pentane isomerization system. Unlike with a pentane isomerization, there is no incentive for lower isomerization reactor temperatures in butane isomerization, so there is not any isomerization unit performance benefit to be gained by doing perchloroethylene decomposition upstream of the isomerization reactor. In the preferred perchloroethylene decomposition reactor on the C5 drag stream there is a ~nil exotherm due to trace ppm perchloroethylene levels and the reactor can be run liquid phase which allows more flexibility on reactor pressure and integration with the rest of the complex. Using an upfront perchloroethylene decomposition reactor using makeup hydrogen for dilution may be constrained in operating temperatures in some cases where the makeup hydrogen feed composition leads to additional exothermic reactions; PERC decomposition on the C5 drag will not be constrained in this way.

The FIG. shows the processing scheme of the present invention. The butane isomerization/deisobutanizer is shown with incorporation of an HCl absorber for recovery & recycle of HCl from the stabilizer offgas and including a chloride guard bed for treatment of the HCl remaining in the combined net offgas.

The C5 drag stream containing 20-100 wppm perchloroethylene, or about 20 to 50 wppm, is combined with hydrogen. Under anticipated reactor conditions the reactor would be operating a 100% liquid phase with dissolved hydrogen. Excess hydrogen is minimized. A Pd or Pt catalyst, as are known to those skilled in the art, is used as being effective for hydrodechlorination. The organic chloride decomposition reactor effluent is sent to a flash drum to strip out hydrogen and HCl from the C5 hydrocarbon stream and thereby providing a chloride-free C5 product plus byproducts such as ethylene and ethane. The HCl-containing flash drum vapor is preferably sent to a HCl absorber where this HCl can be recovered & recycled to the butane isomerization reactor. Direct injection of the flash drum hydrogen and HCl into the HCl absorber liquid bottoms product would eliminate loss of any hydrogen from this stream to the HCl absorber off gas stream. If there is no HCl absorber installed the hydrogen and HCl from the flash drum could be sent to existing offgas caustic treating. Alternately, the perchloroethylene decomposition reactor effluent can be sent to a small chloride guard bed or to a basic resin guard bed for removal of the trace HCl.

The FIG. shows the above described process in more detail. A butane stream 102 containing a mixture of normal butanes and isobutanes is first sent to a deisobutanizer column 110 which produces an isobutane stream 115 exiting the top of the column and a bottoms stream 120 that contains a mixture of hydrocarbons including C5s as well as about 20 to 100 wppm perchloroethylene (PERC), or about 20 to 50 wppm. Bottoms stream 120 passes pump 125 to stream 135. Stream 130 containing hydrogen is mixed with stream 135 heated by heater or heat exchanger 140 and heated stream 145 is sent to organic chloride decomposition reactor 150 to produce a stream 155 containing hydrogen and HCl as well as hydrocarbons including normal C5s and iso-C5s. Stream 155 may be sent in stream 170 to a chloride guard bed 175 with a purified stream 180 recombined with stream 155. Stream 155 then is sent to flash drum 160 with a net C5 stream 165 produced and a gas stream 195 containing hydrogen and HCl that is recycled for use in the isomerization process. Gas stream 195 is shown either being sent in line 200 to line 210 to be combined with normal C4 exiting HCl absorber 190 in bottoms stream 205. The desired isobutanes are produced by the twin butane isomerization reactors 240 and 250. A butane stream 355 exits deisobutanizer column 110 through pump 360 to stream 365 with organic chloride stream 350 and hydrogen stream 340 being added to stream 365 that then enters a first butane isomerization reactor 240 with the product stream 255 that passes through heat exchanger 260 with product stream 265 to then enter a second butane isomerization reactor 250 with the butanes and impurities in stream 270 going to stabilizer 275. A butane stream 335 containing both normal and iso-butanes is then sent to deisobutanizer column 110. An upper stream 280 is sent to heat exchanger 285 with stream 290 being sent through flash drum 295 to produce a C4 LPG stream 300 and a gas stream 305 that is split with about 85 wt % going in stream 185 to HCl absorber 190 to be treated as stated above. A smaller portion or about 15 wt % of gas stream 305 is sent to a chloride guard bed 310 with a cleaned stream 315 exiting that contains mainly hydrogen and mainly C1 to C3 hydrocarbons. A portion of cleaned stream 315 is recycled in stream 320 to compressor 325 to line 330. Also shown is stream 370 that is cooled by cooler 375 to be sent to HCl absorber 190 to remove HCl as needed. Stream 220 is sent through cooler 225 to flash drum 230 to produce a gas stream 380 and a liquid stream 235. Gas stream 380 is sent to chloride guard bed 310. Liquid stream 235, which is mainly normal butanes, can be sent to stream 220 where it flows reverse flow into HCL absorber 190, or it can be combined with butane stream 355.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by mole, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

Any of the above conduits, unit devices, scaffolding, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

Specific Embodiments

While the following is described in conjunction with specific embodiments, it will be understood that this description is intended to illustrate and not limit the scope of the preceding description and the appended claims.

A first embodiment of the invention is a process for producing i-butane comprising sending a feed stream comprising butanes, hydrogen and an organic chloride to a butane isomerization reactor containing an isomerization catalyst to convert a portion of normal butanes in the feed stream to iso-butanes in an isomerized stream; then sending the isomerized stream to a stabilizer column to produce a butane stream containing normal, iso-butanes and C5 hydrocarbons; sending the butane stream to a deisobutanizer column to produce an isomerized upper stream and a bottoms stream comprising a mixture of butanes, C5 hydrocarbons and the organic chloride; and sending the bottoms stream to an organic chloride decomposition reactor to produce an organic chloride decomposition stream comprising hydrogen and HCl. An embodiment of the invention is one, any or all of prior embodiments in this paragraph up through the first embodiment in this paragraph wherein the organic chloride is perchloroethylene. An embodiment of the invention is one, any or all of prior embodiments in this paragraph up through the first embodiment in this paragraph further comprising sending the organic chloride decomposition stream through a chloride guard bed to remove HCl. An embodiment of the invention is one, any or all of prior embodiments in this paragraph up through the first embodiment in this paragraph further comprising sending the organic chloride decomposition stream through a flash drum to recycle hydrogen and HCl. An embodiment of the invention is one, any or all of prior embodiments in this paragraph up through the first embodiment in this paragraph wherein the mixture of butanes, C5 hydrocarbons and organic chloride comprises 20-100 wppm perchloroethylene. An embodiment of the invention is one, any or all of prior embodiments in this paragraph up through the first embodiment in this paragraph wherein hydrogen is added to the bottoms stream before the bottoms stream enters the organic chloride decomposition reactor. An embodiment of the invention is one, any or all of prior embodiments in this paragraph up through the first embodiment in this paragraph wherein the organic chloride decomposition reactor contains a Pd or a Pt containing catalyst. An embodiment of the invention is one, any or all of prior embodiments in this paragraph up through the first embodiment in this paragraph wherein the organic chloride decomposition stream further comprises ethylene, ethylene chloride and ethane. An embodiment of the invention is one, any or all of prior embodiments in this paragraph up through the first embodiment in this paragraph wherein the isomerized upper stream comprises iso-butanes. An embodiment of the invention is one, any or all of prior embodiments in this paragraph up through the first embodiment in this paragraph, further comprising at least one of sensing at least one parameter of the process and generating a signal from the sensing; sensing at least one parameter of the process and generating data from the sensing; generating and transmitting a signal; generating and transmitting data.

The invention claimed is:

1. A process for producing i-butane comprising:
    sending a feed stream comprising butanes, hydrogen and an organic chloride to a butane isomerization reactor containing an isomerization catalyst to convert a portion of normal butanes in said feed stream to iso-butanes in an isomerized stream;
    sending said isomerized stream to a stabilizer column to produce a butane stream containing normal, iso-butanes and C5 hydrocarbons; and sending said butane stream to a deisobutanizer column to produce an isomerized upper stream comprising isobutanes, an NC4 rich side draw stream, and a bottoms stream comprising a mixture of butanes, C5 hydrocarbons and said organic chloride; and sending said bottoms stream to an organic chloride decomposition reactor to produce an organic chloride decomposition stream comprising hydrogen and HCl.

2. The process of claim 1 wherein said organic chloride is perchloroethylene.

3. The process of claim 2 wherein said organic chloride decomposition stream further comprises ethylene, ethylene chloride and ethane.

4. The process of claim 1 further comprising sending said organic chloride decomposition stream through a chloride guard bed to remove HCl.

5. The process of claim 1 further comprising sending said organic chloride decomposition stream through a flash drum to recycle hydrogen and HCl.

6. The process of claim 1 wherein said mixture of butanes, C5 hydrocarbons and organic chloride comprises 20-100 wppm perchloroethylene.

7. The process of claim 1 wherein hydrogen is added to said bottoms stream before said bottoms stream enters said organic chloride decomposition reactor.

8. The process of claim 1 wherein said organic chloride decomposition reactor contains a Pd or a Pt containing catalyst.

9. The process of claim 1, further comprising at least one of:

sensing at least one parameter of the process and generating a signal from the sensing and optionally further transmitting the signal; and sensing at least one parameter of the process and generating data from the sensing and optionally further transmitting the data.

* * * * *